(12) United States Patent
Bethke et al.

(10) Patent No.: US 9,021,874 B2
(45) Date of Patent: May 5, 2015

(54) APPARATUS AND METHOD FOR TESTING THE ADHESIVE STRENGTH OF A COATING ON A SUBSTRATE

(75) Inventors: Reinhold Bethke, Wolfenbüttel (DE); Michael Eder, Braunschweig (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 116 days.

(21) Appl. No.: 13/805,065

(22) PCT Filed: Jun. 15, 2011

(86) PCT No.: PCT/EP2011/059910
§ 371 (c)(1),
(2), (4) Date: Jan. 23, 2013

(87) PCT Pub. No.: WO2011/157739
PCT Pub. Date: Dec. 22, 2011

(65) Prior Publication Data
US 2013/0112005 A1 May 9, 2013

(30) Foreign Application Priority Data

Jun. 18, 2010 (DE) .......................... 10 2010 030 260

(51) Int. Cl.
*G01N 19/04* (2006.01)
*G01N 3/42* (2006.01)
*G01N 35/04* (2006.01)

(52) U.S. Cl.
CPC .................. *G01N 19/04* (2013.01); *G01N 3/42* (2013.01); *G01N 35/04* (2013.01); *G01N 2203/0062* (2013.01); *G01N 2203/0098* (2013.01); *G01N 2203/0226* (2013.01)

(58) Field of Classification Search
CPC ............ G01N 3/42; G01N 2203/0226; G01N 2203/0062
USPC .................................................. 73/81, 83, 799
See application file for complete search history.

(56) References Cited

U.S. PATENT DOCUMENTS 3,738,160 A * 6/1973 Sobajima .......................... 73/81
5,602,329 A * 2/1997 Haubensak ....................... 73/82

(Continued)

FOREIGN PATENT DOCUMENTS

DE 40 18 333 A1 12/1991
DE 40 22 382 A1 1/1992

(Continued)

OTHER PUBLICATIONS

Machine Translation of DE 4022382, Date: Jan. 1992, Publisher of Translation: Google, pp. 1-6.*

(Continued)

*Primary Examiner* — Harshad R Patel
(74) *Attorney, Agent, or Firm* — Brinks Gilson & Lione

(57) ABSTRACT

A device for testing the adhesive strength of a coating on a substrate, containing a unit for generating mechanical stress in a predefinable surface area of the coating and an evaluation system, which contains a unit for image acquisition and a unit for evaluating the cracks that occur, wherein the device further contains a transport unit, by which the substrate can be moved at least from the unit for generating mechanical stress to the evaluation system, and a heating unit, by which the substrate can be heated to a predefinable temperature.

18 Claims, 2 Drawing Sheets

(56) References Cited

U.S. PATENT DOCUMENTS

| | | | |
|---|---|---|---|
| 6,134,954 | A | 10/2000 | Suresh et al. |
| 6,247,355 | B1 | 6/2001 | Suresh et al. |
| 2003/0058417 | A1 | 3/2003 | Nagahashi |
| 2008/0028840 | A1 | 2/2008 | Smith et al. |
| 2010/0212411 | A1 | 8/2010 | Passilly et al. |

FOREIGN PATENT DOCUMENTS

| | | | | | |
|---|---|---|---|---|---|
| DE | 4022382 | A1 | * | 1/1992 | ............ G01N 3/40 |
| DE | 196 01 239 | A1 | | 7/1996 | |
| DE | 199 50 310 | A1 | | 4/2001 | |
| DE | 100 43 155 | A1 | | 3/2002 | |
| FR | 2 907 899 | | | 5/2008 | |
| GB | 1 214 865 | | | 12/1970 | |
| GB | 1 214 866 | | | 12/1970 | |
| GB | 1214866 | A | * | 12/1970 | ............ G01N 3/40 |
| LU | 88821 | A1 | | 4/1998 | |

OTHER PUBLICATIONS

"Coating of Cold Forging Tools" Association of German Engineers, VDI 3198 Aug. 1992.

DE Office Action re Original mit Anlagen and Fristsetzung folgt Mar. 21, 2011.

International Preliminary Report with English Translation, dated Jan. 3, 2013, pp. 1-24, International Application No. PCT/EP2011/059910, International Bureau of WIPO, Geneva, Switzerland.

* cited by examiner

APPARATUS AND METHOD FOR TESTING THE ADHESIVE STRENGTH OF A COATING ON A SUBSTRATE

BACKGROUND

The invention relates to an apparatus for testing the adhesive strength of a coating on a substrate, comprising a device for generating mechanical stress in a predefinable surface region of the coating, and an evaluation unit which comprises a device for image acquisition and a device for assessing the cracks which arise. The invention further relates to a method for testing the adhesive strength of a coating on a substrate, in which method, in a first method step, mechanical stress is applied to at least one predefinable surface region of the coating, and, in a second method step, the surface region is investigated for damage by means of an evaluation unit.

Coatings can be applied to substrates by a multiplicity of methods which are known per se. The coating can increase the mechanical or thermal load-bearing capacity of the substrate or can serve for decorative purposes. To ensure reliable operation, a sufficient adhesive strength of the coating on the substrate is required. Thus, methods of the type mentioned in the introduction are used for testing and assessing the adhesive strength in the development of novel coatings or for quality assurance during the manufacture of coated components.

A method of the type mentioned in the introduction is known from DE 100 43 155 A1. According to this known method, a partial region of the coating is loaded by means of a test specimen. Then, the crack pattern which arises around the impression of the test specimen and the area content of released regions are investigated by means of an optical microscopy image.

However, this known method has the disadvantage that the coated substrate has to be transported between the loading with the test specimen and the optical microscope. This makes an additional working step necessary, which reduces the efficiency of the method. Furthermore, substrates may be mixed up and/or there may be a mix up between a plurality of test impressions applied to a substrate. This reduces the reliability of the method.

If the coated substrate is to be used at elevated operating temperatures, the adhesive strength of the coating may be higher or even lower on account of different coefficients of thermal expansion between the base material and the coating at relatively high temperatures. Therefore, it is necessary to test and assess the adhesive strength at the planned operating temperature. This requires that the loading by the test specimen and the evaluation by optical microscopy are effected at a uniform temperature in order to avoid thermal stresses during the measurement. As a result, the known method requires the substrate which is at an elevated temperature to be transported, which is technically complex and dangerous for the operating personnel.

The invention is therefore based on the object of developing a measurement method of the type mentioned in the introduction in such a way that the measurement can be made in a more reliable and simple manner. A further aim is to make it possible to carry out the measurement at an elevated temperature.

SUMMARY

According to the invention, it is proposed to spatially arrange a device for generating mechanical stress in a predefinable surface region of the coating and an evaluation unit in such a way that the coated substrate can be moved between the evaluation unit and the device for generating the mechanical stress by means of a transport device. According to the invention, it is proposed in this respect to firstly apply mechanical stress of a predefinable magnitude in a predefinable surface region of the coating, to then release it again and to then bring the surface region into the acquisition region of the evaluation unit. Transportation under an applied load or mechanical stress therefore does not take place. In this way, it is possible for the substrate to be transferred in an automated manner and therefore quickly and reliably. It is thus possible to avoid a mix up of various substrates or a mix up of various test sites on a substrate.

According to the invention, it is proposed that the test impression be evaluated in an automated manner. To this end, an image acquisition device is available, which can comprise, for example, a CCD camera or another image converter known per se. The image of the test impression which is created can then be fed to a device for assessing the cracks which arise in the evaluation device. In some embodiments of the invention, the device for assessing the cracks which arise can determine a number and/or length of the cracks. To this end, the device for assessing the cracks which arise may comprise a software which is executed on a microprocessor or a microcontroller. In addition, the evaluation device can perform further assessments of the test impression in an automated manner in order to determine the adhesive strength.

In some embodiments of the invention, the apparatus may comprise a control device which is designed to control the device for generating mechanical stress in a predefinable surface region of the coating and the transport device sequentially, such that transportation under an applied load or mechanical stress is avoided. In this way, the predefinable surface region always has an approximately punctiform extent rather than a linear extent.

In some embodiments of the invention, the transport device may comprise at least one linear guide. Such a linear guide makes it possible in an easy manner to transfer the substrate between the device for generating mechanical stress and the evaluation unit. To this end, the linear guide may have a mechanical or hydraulic drive. In some embodiments, the drive may be effected by a threaded rod by means of a stepper motor.

This makes it possible to position the substrate in an accurate and reproducible manner. In some embodiments, it is possible to use a plurality of linear guides in order to make it possible to position the substrate in a plurality of spatial directions. In some embodiments, it may be provided that two orthogonal linear guides make it possible to position the substrate in the x and y directions.

In some embodiments of the invention, the apparatus may further comprise a heating device, by means of which the substrate can be brought to a predefinable temperature. The heating device can feed a heating power by means of electrical or chemical energy to the substrate to be investigated, which brings the substrate to a temperature which can correspond to the planned operating temperature. In other embodiments of the invention, the temperature may also be higher or lower than the operating temperature. In this way, it is possible to assess the adhesive strength at the planned operating temperature, and it is thereby possible to make a more reliable statement about the adhesive strength of the coating under the planned operating conditions. To this end, in some embodiments provision may be made of a regulating device, by means of which the predefinable temperature can be kept within a predefinable tolerance. The regulating device can comprise a PI, a PD or a PID regulator, with which the thermal energy fed to the substrate is controlled. The reliability of the measurement is increased further in this way.

In one embodiment of the invention, the evaluation unit may comprise an optical microscope. In a manner known per se, it is therefore possible for the area content of the released area and/or the number of cracks on the periphery of the loaded surface region or the average crack length to be determined by subjective assessment by the operating personnel. In some embodiments of the invention, the optical microscope may be connected to an electronic image converter, for example to a CCD camera. The image from the optical microscope can thereby be fed to an area determination device and/or to a counting device and/or to a measuring device, which makes it possible to objectively assess the surface region subjected to the mechanical stress. In some embodiments of the invention, the area determination device and/or the counting device and/or the measuring device may be realized in the form of a software.

In some embodiments of the invention, the apparatus may further comprise a control device, by means of which a plurality of surface regions on the substrate can be selected. In addition to the selection of a surface region which is subjected to mechanical stress by loading, the control device may also perform the automated positioning of said surface region in the acquisition region of the evaluation unit. Particularly if the measurement method is carried out repeatedly in different surface regions, this makes it possible to reliably assign the test impressions to the measurement results obtained by the evaluation unit. Instances of mixing up samples and/or test impressions can be avoided in this way by the use of the control device.

In some embodiments of the invention, the apparatus may further comprise a heat shield device. The heat shield device may serve for protecting the surrounding area and/or the user of the apparatus from elevated temperatures. Furthermore, the heat shield device may have at least one surface region which is formed so as to be optically transparent, in order to make it possible for the substrate or the predefinable surface region to be acquired by the evaluation unit.

BRIEF DESCRIPTION OF THE DRAWINGS

In the text which follows, the invention will be explained in more detail with reference to an exemplary embodiment and with reference to figures without limiting the general concept of the invention. In the figures.

DESCRIPTION OF PREFERRED EMBODIMENTS

Figure 1:
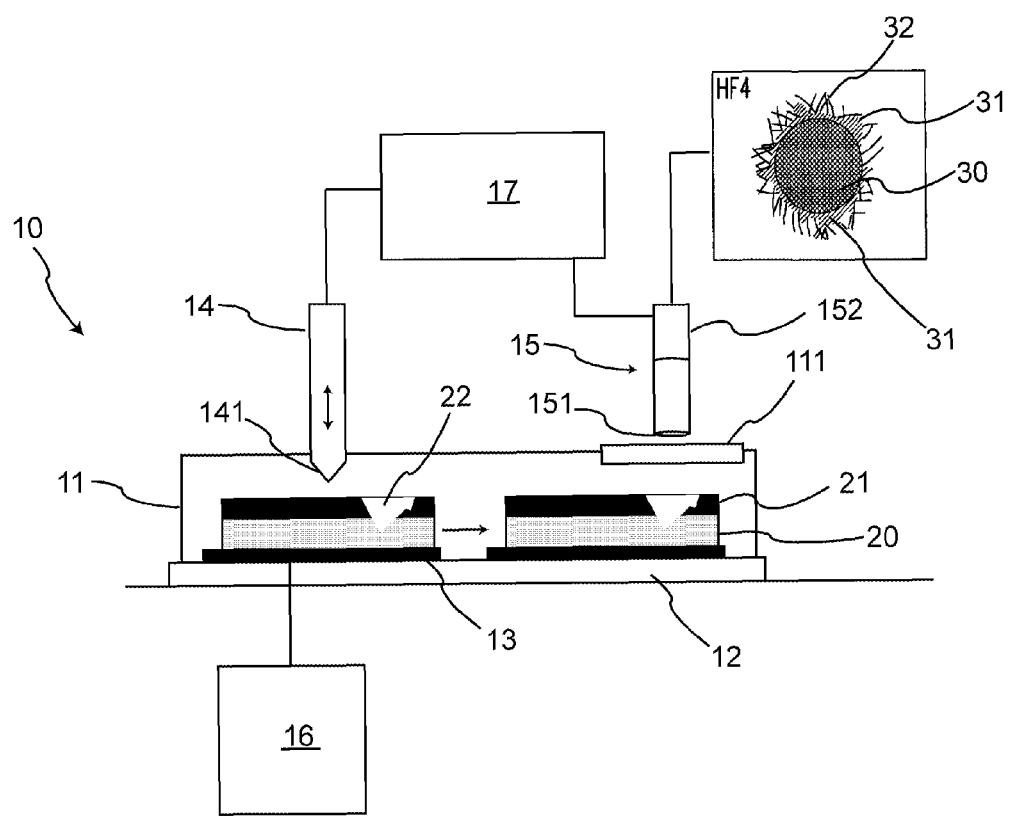
FIG. 1 shows the schematic design of a proposed apparatus.

FIG. 1 shows an apparatus for testing the adhesive strength of a coating according to the present invention. FIG. 1 shows by way of example a substrate 20 with a coating 21 applied thereto. In some embodiments of the invention, the substrate 20 may be a machine element, for example an abrasive ring, a bearing shell, a shaft, a bearing bushing, a cutting edge, a turbine blade or vane or any other desired component subject to mechanical and/or thermal loading.

A coating 21 having either a decorative function or a protective function is applied to the substrate 20. By way of example, the coating 21 may be a thermal barrier layer or a tribologically loaded layer. In some embodiments, the coating 21 may also be a sensor layer. The coating 21 can be applied to the substrate 20 by means of vapor deposition, by electroless deposition or electrodeposition or in another way. The coating may comprise a hard material, for example carbon or ceramic. The coating can have a thickness of more than 3 µm. In some embodiments, the coating may comprise a layer system consisting of a plurality of individual layers. The invention does not teach the use of a specific coating as the principle of the solution.

In order that the coating 21 does not unintentionally become detached during operation of the substrate or structural element 20, it is necessary for there to be a sufficient adhesive strength between the coating and the substrate. The adhesive strength is tested by means of the apparatus 10 according to the invention.

For testing, mechanical stress is generated in a predefinable surface region 22 of the coating 21 by means of a device 14. In some embodiments, the device 14 may have a probe tip 141. The probe tip can have a radius of between 0.1 mm and 1 mm. The probe tip 141 may consist of a hard material, for example diamond, diamond-like carbon or a ceramic. In some embodiments of the invention, a ceramic may comprise a nitride, an oxide or a carbide. The device 14 can be moved onto the surface of the coating 21 along the arrow indicated. To this end, in some embodiments of the invention it is possible for mechanics or hydraulics (not shown in FIG. 1) to be provided, these applying a predefinable force to the probe tip 141. In some embodiments of the invention, the probe tip 141 and the applied force can be selected in such a way that the apparatus implements a Rockwell C test pursuant to DIN 50103.

After the surface region 22 has been mechanically loaded, the substrate 20 is moved into the acquisition region of the evaluation unit 15 by means of the transport device 12. The evaluation unit 15 comprises an optical acquisition system 151 and also a device 152 for electronic image processing. The device 152 comprises on the one hand an electronic image converter, for example a CCD camera. Furthermore, the evaluation unit 15 may comprise an area determination device for determining the released area and/or a counting device for determining the number of cracks and/or a measuring device for determining the average crack length. In this way, the evaluation unit 15 can achieve, by means of electronic image processing, an objectifiable measurement result of the surface region 22 which is largely unaffected by subjective influences of the test personnel.

In the top part of the image in FIG. 1 on the right-hand side, a possible test result is shown schematically. The figure shows a surface region 22 in plan view. The central test indentation 30 which has been brought about by the probe tip 141 can be seen. The figure further shows released regions 31, in which the coating 21 has undergone complete spalling and the base material 20 has become visible. In addition, the figure shows cracking 32 at the edge of the test indentation 30. By determining the size of the released area 31 and/or by determining the number of cracks on the periphery of the test indentation 30 and/or by measuring the average crack length, it is possible to determine the extent of the damage and from this to determine the adhesive strength of the coating 21 on the substrate 20. In some embodiments of the invention, the damage pattern can be assessed pursuant to the VDI guideline 3198.

In order to assess the adhesive strength of the coating 21 in different surface regions, the probe tip 141 can load a plurality of surface regions 22. In this case, each test indentation can be acquired by the evaluation unit 15 immediately after it has been created, such that the substrate 20 is repeatedly transferred between the two positions shown in FIG. 1. In other embodiments of the invention, firstly a plurality of surface regions 22 can be selected and loaded by the device 14, in order to then carry out an assessment of the plurality of surface regions 22. In this way, only a single transfer of the substrate 20 by means of the transport device 12 is required.

In some embodiments of the invention, the transport device 12 can move the substrates 20 into further positions (not shown), for example a charging and/or removal position or a production position. In this case, the transport device 12 may be a component part of a relatively large transport system or a production line for coated substrates 20. The transport device 12, the device 14 for generating mechanical stress and/or the evaluation unit 15 can be controlled by a control device 17, which takes on the positioning of the substrates 20 under the device 14 or the evaluation unit 15 and assigns the test results obtained to the respective substrate or the respective predefinable surface region 22 of the substrate 20. To this end, the control device 17 may interact with a database, in which the test results are stored.

In order to make it possible to also test the adhesive strength at a temperature which differs from room temperature, in some embodiments the apparatus 10 may have a heating device 13. The heating device 13 may comprise, for example, an electrical resistance heater, a gas-operated burner, an induction heater or another heat source known per se. The heating device 13 is in contact with the substrate 20, and therefore the heat generated in the heating device 13 is passed to the substrate 20. According to the present invention, the contact can be made by heat conduction or by heat radiation or by another field. The temperature of the substrate 20 or the temperature of the heating device 13 can be controlled and monitored by means of a regulating device 16. In some embodiments of the invention, the substrate 20 can thereby be heated to a temperature of about 100° C. to about 800° C. The selected temperature can correspond to the later operating temperature of the structural element 20.

In order to avoid endangering the user as a result of the elevated temperature of the substrate 20, in some embodiments of the invention the apparatus may have a heat shield device 11. In some embodiments, the heat shield device 11 may comprise a sheet-metal housing, which is thermally insulated by means of an insulating material. Hard foams or inorganic fiber materials such as, for example, mineral wool can be used as the insulating material. In order to avoid damage to the substrate or the coating by the reaction with atmospheric oxygen or nitrogen, in some embodiments of the invention the interior of the heat shield device 11 can be flushed with a protective gas or evacuated. In some embodiments, the protective gas may comprise a noble gas such as helium or argon.

In order to make it possible for the evaluation unit 15 to optically acquire the surface region 22, the heat shield device 11 may have a surface region 111 which is at least partially transparent in the optical spectral range. In order to protect the evaluation unit 15 from thermal loading, the surface region 111 may have an infrared reflecting coating. In some embodiments of the invention, the surface region 111 may comprise a window, which is configured to be at least partially opaque in the infrared spectral range and to be at least partially transparent in the optical spectral range.

Figure 2:
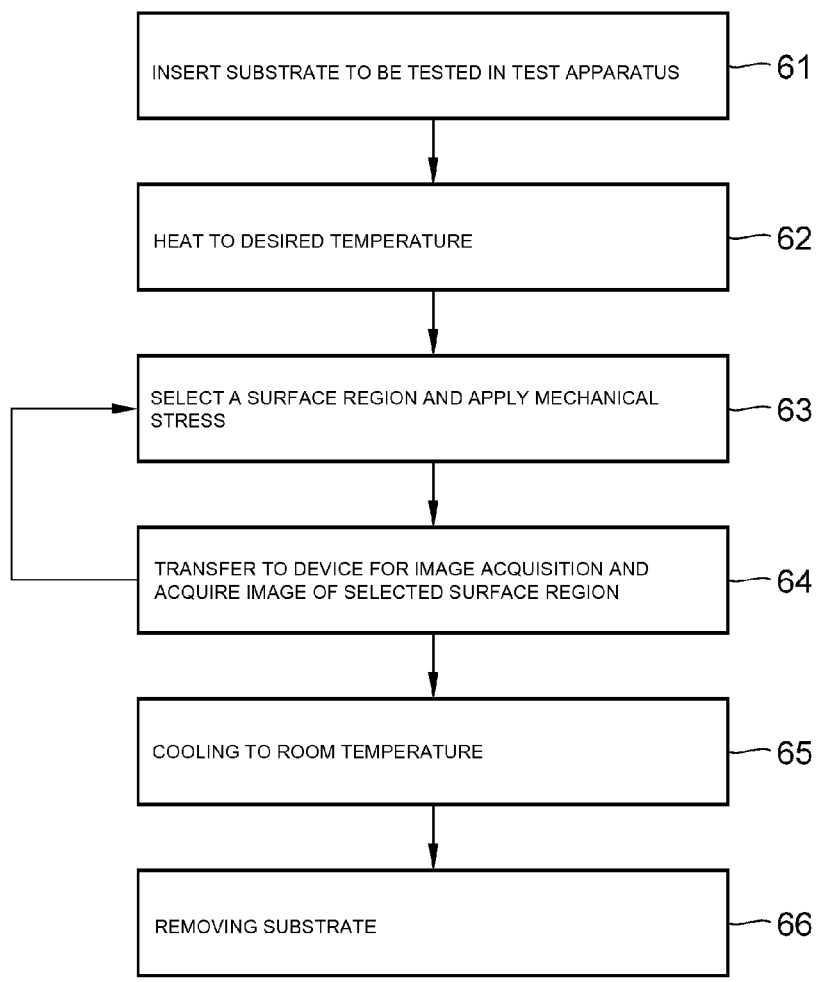
FIG. 2 shows the sequence of a measurement method according to the invention.

FIG. 2 shows a flow chart illustrating the sequence of the method proposed according to the invention. In the first method step 61, a substrate 20 to be tested with a coating applied thereto is inserted into the proposed apparatus 10 or applied to the heating element 13.

In the following method step 62, the substrate 20 is brought to a desired measurement temperature, which, in some embodiments of the invention, can be monitored by the regulating device 16. If the measurement temperature corresponds to room temperature or to the temperature which the substrate is at from the preceding method step, method step 62 may also be omitted.

As soon as the substrate 20 has reached the intended temperature, in method step 63 a surface region 22 is selected and mechanical stress is exerted on said surface region 22 by means of the device 14. Once the surface region 22 has been loaded by the device 14, the acting force is withdrawn and the probe tip 141 is lifted from the surface of the coating 21. In some embodiments of the invention, the surface region 22 may be defined or selected with the aid of the evaluation unit 15.

Then, in method step 64, the substrate 20 is transferred into the acquisition region of the evaluation unit 15. In the evaluation unit 15, the surface region 22 is optically acquired and the size of the released area 31 and/or the number of cracks 32 and/or the average crack length are determined. Once method step 64 has been concluded, it is possible to make a statement about the adhesive strength of the coating 21 on the substrate 20. In some embodiments of the invention, method steps 63 and 64 can also be repeated several times in order to examine different surface regions 22. In this way, it is possible to determine the distribution of the adhesive strength over the surface of the substrate 20.

After the measurement method has been carried out for the last time, in method step 65 the substrate 20 is cooled again to room temperature in order to avoid dangerous handling of the substrate 20 or damage as a result of oxidation. In order to accelerate the cooling, it may be provided in method step 65 to provide a cooling gas flow or to bring the substrate 20 into contact with a heat sink.

Finally, the substrate 20 can be removed from the apparatus 10 in method step 66. The apparatus 10 is then ready for the method to be carried out again.

It goes without saying that the invention is not limited to the embodiments shown in the figures. The above description is therefore not to be considered as having a limiting effect, but rather as explanatory. The claims which follow are to be understood in such a way that a feature indicated is present in at least one embodiment of the invention. This does not preclude the presence of further features. Where the claims and the above description define "first" and "second" features, this designation serves to distinguish between two features of the same type, without defining a ranking.

The invention claimed is:

1. An apparatus for testing the adhesive strength of a coating on a substrate, comprising
   a device configured to generate mechanical stress in a predefinable surface region of the coating,
   an evaluation unit, and
   a transport device configured to move the substrate at least from the device for generating mechanical stress to the evaluation unit, wherein
   the evaluation unit comprises an electronic image processing device configured to acquire an image and a device configured to assess cracks which arise in the coating, wherein
   said device configured to assess the cracks comprises any of a counting device configured to determine the number of cracks being located at a circumference of said predefinable surface region and/or a measuring device configured to measure the length of at least one crack from the image acquired.

2. The apparatus according to claim 1, wherein the transport device comprises at least one linear guide.

3. The apparatus according to claim 1, further comprising a heating device configured to heat the substrate to a predefinable temperature.

4. The apparatus according to claim 3, further comprising a first control device configured to keep the predefinable temperature constant within a predefinable tolerance.

5. The apparatus according to claim 3, further comprising a heat shield device.

6. The apparatus according to claim 1, wherein the evaluation unit further comprises an area calculation unit configured to determine the size of flaked subareas being located adjacent to the circumference of said predefinable surface region.

7. The apparatus according to claim 1, further comprising a second control device configured to select a plurality of surface regions to be tested.

8. An apparatus for testing the adhesive strength of a coating on a substrate, comprising
   a device configured to generate mechanical stress in a predefinable surface region of the coating,
   a computer based evaluation unit, and
   a transport device configured to move the substrate at least from the device configured to generate mechanical stress to the computer based evaluation unit, wherein
   the computer based evaluation unit is configured to determine the adhesive strength, comprising an electronic image processing device configured to acquire an image and a device configured to analyse cracks which arise in the coating, wherein
   said device configured to analyse the cracks comprises any of a counting device configured to determine the number of cracks being located at a circumference of said predefinable surface region and/or a measuring device configured to measure the mean value of the length of the cracks.

9. The apparatus according to claim 8, wherein the transport device comprises at least one linear guide.

10. The apparatus according to claim 8, comprising a heating device configured to heat the substrate to a predefinable temperature and at least one control device configured to keep the predefinable temperature constant within a predefinable tolerance.

11. The apparatus according to claim 8, wherein the evaluation unit further comprises an area calculation unit configured to determine flaked subareas being located adjacent to the circumference of said predefinable surface region.

12. The apparatus according to claim 8, wherein said electronic image processing device comprises an electronic image converter.

13. A method for testing the adhesive strength of a coating on a substrate, said method comprising the following steps:
   applying mechanical stress to at least one predefinable surface region of the coating, and,
   investigating the surface region for damage by an automatic evaluation unit, wherein
   the substrate is moved by a transport device after being subject to mechanical stress and before investigation, and
   the investigating comprises acquiring an image of the at least one predefinable surface region and providing said image to the automatic evaluation unit, and
   any of determining the number of cracks being located at a circumference of said predefinable surface region and/or measuring the mean value of the length of the cracks with said automatic evaluation unit.

14. The method according to claim 13, wherein testing the adhesive strength is done at a substrate temperature between 100° C. and 800° C.

15. The method according to claim 14, wherein the temperature of the substrate remains constant within a predefinable tolerance between the method step of applying mechanical stress and the method step of investigating the surface region.

16. The method according to claim 13, further comprising determining the surface area of flaked subareas adjacent to the circumference of said predefinable surface region.

17. The method according to claim 13, wherein a plurality of surface regions are selected and the method steps applying mechanical stress and investigating the surface region for damage are carried out repeatedly.

18. The method according to claim 13, wherein the substrate is not moved while mechanical stress is being applied to a predefinable surface region of the coating.

\* \* \* \* \*